US012636002B2

(12) United States Patent
Holloway

(10) Patent No.: US 12,636,002 B2
(45) Date of Patent: May 26, 2026

(54) SURGICAL RETRACTOR

(71) Applicant: Daniel Holloway, Rocky View County (CA)

(72) Inventor: Daniel Holloway, Rocky View County (CA)

( * ) Notice: Subject to any disclaimer, the term of this patent is extended or adjusted under 35 U.S.C. 154(b) by 97 days.

(21) Appl. No.: 18/635,281

(22) Filed: Apr. 15, 2024

(65) Prior Publication Data

US 2025/0318822 A1     Oct. 16, 2025

(51) Int. Cl.
    *A61B 17/02*         (2006.01)
    *A61B 17/00*         (2006.01)
(52) U.S. Cl.
    CPC ..................... *A61B 17/0293* (2013.01); *A61B 2017/00557* (2013.01); *A61B 2017/00862* (2013.01); *A61B 2017/0237* (2013.01)
(58) Field of Classification Search
    CPC ........... A61B 2017/00557; A61B 2017/00862; A61B 17/0218; A61B 2017/0225; A61B 2017/0237
    USPC ................ 600/184–245; 606/246–279, 86 A
    See application file for complete search history.

(56) References Cited

U.S. PATENT DOCUMENTS

| | | | | | |
|---|---|---|---|---|---|
| 3,782,370 | A | * | 1/1974 | McDonald ......... | A61B 17/0293 600/207 |
| 5,810,721 | A | * | 9/1998 | Mueller ............. | A61B 17/0293 600/206 |
| 6,277,136 | B1 | * | 8/2001 | Bonutti .............. | A61B 17/0218 606/190 |
| 7,294,103 | B2 | * | 11/2007 | Bertolero ........... | A61B 17/3423 600/206 |
| 2003/0199737 | A1 | * | 10/2003 | Deslauriers .............. | A61B 1/32 600/207 |
| 2010/0312066 | A1 | * | 12/2010 | Cropper ............. | A61B 17/3423 600/207 |
| 2011/0201894 | A1 | * | 8/2011 | O'Prey .............. | A61B 17/0293 600/219 |

* cited by examiner

*Primary Examiner* — Eduardo C Robert
*Assistant Examiner* — Tara Rose E Carter
(74) *Attorney, Agent, or Firm* — Lewellyn Law, PLLC; Stephen Lewellyn

(57)                ABSTRACT

A surgical retractor has proximal and distal ends and an intermediate portion. The proximal and distal ends each have an inflatable annular ring. The intermediation portion has flexible sheath that is attached it its opposite ends to a respective annular ring. An access opening extends through the rings and the sheath along a longitudinal axis extending through the distal and proximal ends. The first and second inflatable annular rings are configured to expand radially from the longitudinal axis without expanding axially. The flexible sheath is configured to expand radially from the longitudinal axis without expanding axially.

12 Claims, 6 Drawing Sheets

SURGICAL RETRACTOR

FIELD OF THE INVENTION

The invention relates to surgical retractor devices, and more specifically to retractor devices intended to facilitate minimally invasive cardiac or thoracic surgery by providing both soft tissue and bone retraction in a single device.

BACKGROUND OF THE INVENTION

Cardiac or thoracic surgery can include various operations in the chest. Surgery inside the chest requires an incision through the muscle and/or bone. It is often essential to use one or more retractors to spread soft tissues such as muscle and fascia and bones such as the sternum or ribs. Spreading the tissues and bones creates a space required for visualization of the internal structures and for insertion and manipulation of surgical instruments.

For minimally invasive cardiac surgery performed through a thoracotomy (an incision made between the ribs), most surgeons will use a mechanical rib spreader and a soft tissue retractor. The soft tissue retractor is placed to control the muscle and fat and then the rib spreader is used to spread the ribs enough to enable the surgery to be performed. While soft tissue retractors are usually well tolerated by the patient, rib spreaders can be associated with significant post-surgery pain and morbidity. Mechanical rib spreaders use metal surfaces to push on the ribs, which necessarily also pushes on intercostal muscle and associated neurovascular bundle. Intense focal pressure on the muscles and nerves created by the rigid metal surface of a rib spreader can cause significant post-operative pain. Additionally, localized pressure from the metal surfaces commonly causes rib cracking or fracturing which is associated with pain and bleeding.

Accordingly, there is a need and a desire for a surgical retractor that can provide both soft tissue and bone retraction while minimizing trauma and rib injury.

SUMMARY OF THE INVENTION

In general, this disclosure relates to surgical retractors that include inflatable rings and an interconnecting sheath that is configured to be placed in a thoracic incision to provide both soft tissue and bone retraction while minimizing soft tissue trauma and rib injury.

In an aspect, this disclosure relates to a surgical retractor including inflatable annular rings and a flexible sheath having a proximal end and a distal end, the proximal end attached to a first annular ring and the distal end attached to a second annular ring. An access opening extends through the rings and the sheath along a longitudinal axis extending through the distal and proximal ends. The first and second inflatable annular rings are configured to expand radially from the longitudinal axis without expanding axially. The flexible sheath is configured to expand radially from the longitudinal axis without expanding axially.

In an aspect one or both of the first and second inflatable annular rings may have an inflatable innertube enclosed in an exterior covering.

In an aspect one or both of the first and second inflatable annular rings may have a two-way stretch fabric material having stretch fibers oriented so as to permit the radial expansion without the axial expansion.

In an aspect, one or both of the first and second inflatable annular rings may have an inflatable innertube enclosed in an exterior covering.

In an aspect, the flexible sheath may comprise a two-way stretch fabric material having stretch fibers oriented so as to permit the radial expansion without the axial expansion.

In an aspect one or both of the first and second inflatable annular rings may comprise pleats along a length thereof and wherein the pleats may be constructed so as to permit the radial expansion without the axial expansion.

In an aspect, one or both of the first and second inflatable annular rings may comprise a two-way stretch fabric material having stretch fibers oriented so as to permit the radial expansion without the axial expansion.

In an aspect, one or both of the first and second inflatable annular rings may comprise an inflatable innertube enclosed in an exterior covering and wherein the exterior covering may comprise the two-way stretch fabric material.

In an aspect, this disclosure relates to a surgical retractor having a proximal end, a distal end, a longitudinal axis defining an access opening extending through the proximal and the distal end. The retractor may have first and second non-expanding sides arranged opposite from one another and having a space extending therebetween. The retractor may have first and second expanding sides arranged opposite from one another and extending between the first and second non-expanding sides. Each of the first and second expanding sides may be configured to be extensible to increase the space between the first and second non-expanding sides.

In an aspect, the first and second expanding sides may have a first inflatable element disposed at the proximal end, a second inflatable element disposed at the distal end, and an intermediate portion extending between the first and second inflatable elements and along a length of each; and wherein the first and second inflatable elements may be to extend in length but not in thickness when inflated.

In an aspect, the first inflatable element and the second inflatable element of one or both of the first and second expanding sides may comprise a two-way stretch fabric material having stretch fibers oriented so as to permit the expansion in length without the expansion in thickness.

In an aspect, the intermediate portion of one or both of the first and second expanding sides may comprise a two-way stretch fabric material having stretch fibers oriented so as to permit expansion of the intermediate portion along a direction between the non-expanding sides without expanding in a direction between the first and second inflatable elements.

In an aspect, one or both of the first and second inflatable members of one or both of the first and second expanding sides comprise an inflatable innertube enclosed in an exterior covering.

In an aspect, the exterior covering may comprise a two-way stretch fabric material having stretch fibers oriented so as to permit the expansion in length without the expansion in thickness.

In an aspect, the first and second expanding sides may have a first inflatable element disposed at the proximal end, a second inflatable element disposed at the distal end, and an intermediate portion extending between the first and second inflatable elements and along a length of each; and wherein the first and second inflatable elements are configured to extend in length but not in thickness when inflated; and the first inflatable element and the second inflatable element of one or both of the first and second expanding sides may comprise a two-way stretch fabric material having stretch fibers oriented so as to permit the expansion in length without the expansion in thickness.

In an aspect, the first and second expanding sides may have a first inflatable element disposed at the proximal end, a second inflatable element disposed at the distal end, and an intermediate portion extending between the first and second inflatable elements and along a length of each; and wherein the first and second inflatable elements are configured to extend in length but not in thickness when inflated; and the first inflatable element and the second inflatable element of the first and second expanding sides comprises a two-way stretch fabric material having stretch fibers oriented so as to permit the expansion in length without the expansion in thickness.

In an aspect, one or both of the first and second inflatable members of one or both of the first and second expanding sides may comprise an inflatable innertube enclosed in an exterior covering.

In an aspect, the exterior covering may comprise the two-way stretch fabric material.

In an aspect, the first and second non-expanding sides may be constructed of a rigid material.

Numerous additional objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

For a better understanding of the invention, its operating advantages and the specific objects attained by its uses, reference should be had to the accompanying drawings and descriptive matter in which there are illustrated embodiments of the invention.

BRIEF DESCRIPTION OF THE DRAWINGS

The following drawings illustrate by way of example and are included to provide a further understanding of the invention for the purpose of illustrative discussion of the embodiments of the invention. No attempt is made to show structural details of the embodiments in more detail than is necessary for a fundamental understanding of the invention, the description taken with the drawings making apparent to those skilled in the art how the several forms of the invention may be embodied in practice. Identical reference numerals do not necessarily indicate an identical structure. Rather, the same reference numeral may be used to indicate a similar feature or a feature with similar functionality. In the drawings.

DETAILED DESCRIPTION

Figure 1:
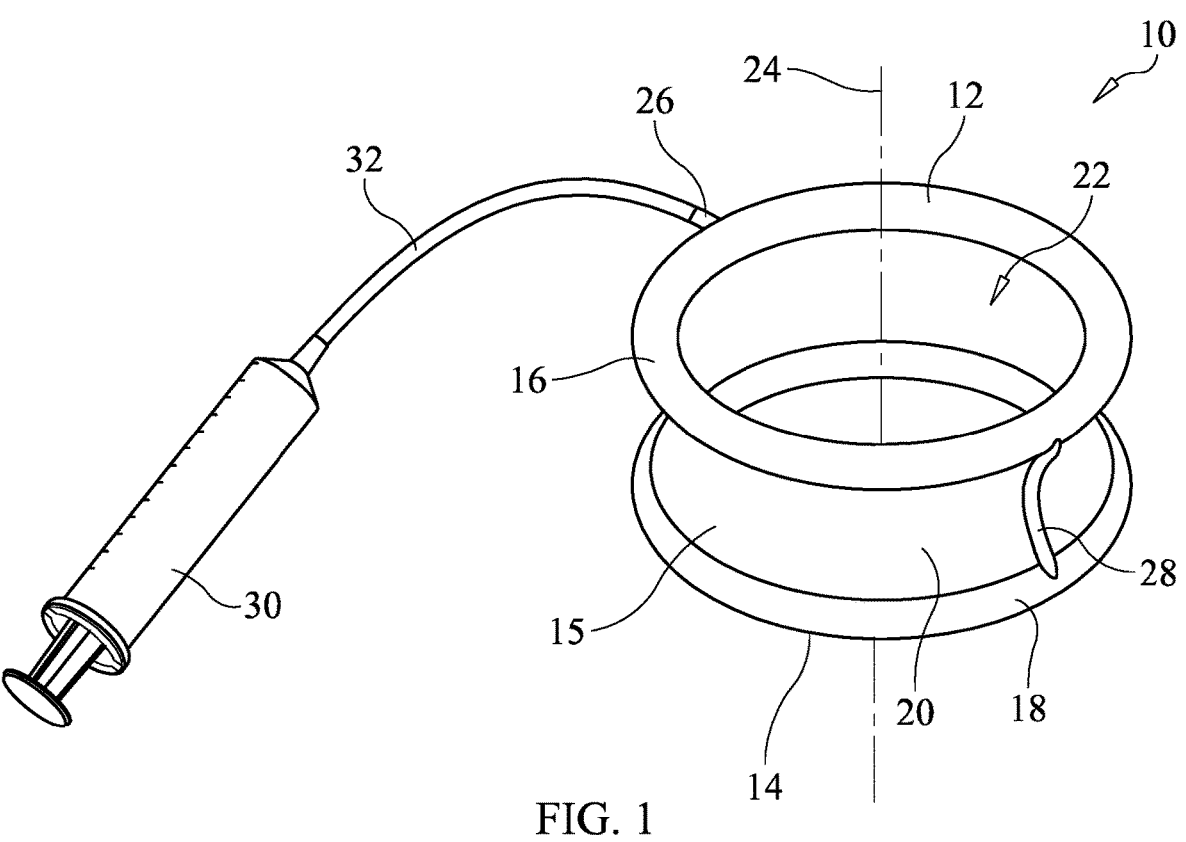
FIG. 1 is a perspective view of a surgical retractor shown in accordance with an embodiment of the invention.
Figure 2:
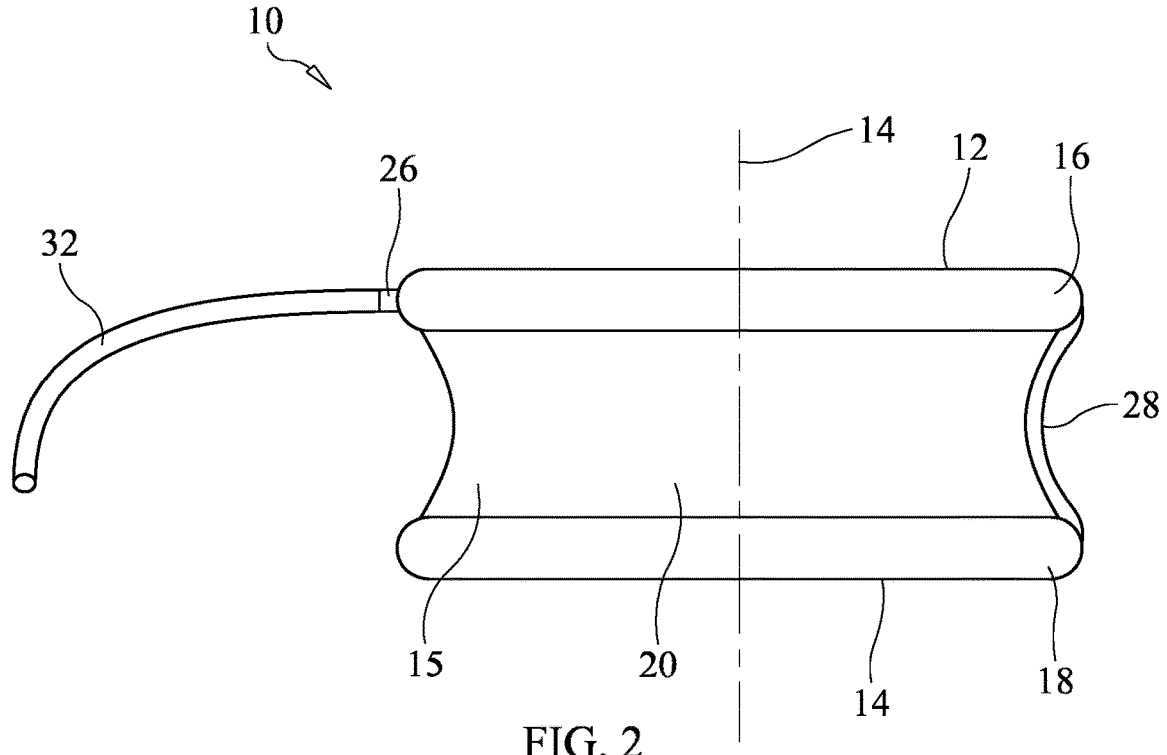
FIG. 2 side view of the surgical retractor of FIG. 1.
Figure 3:
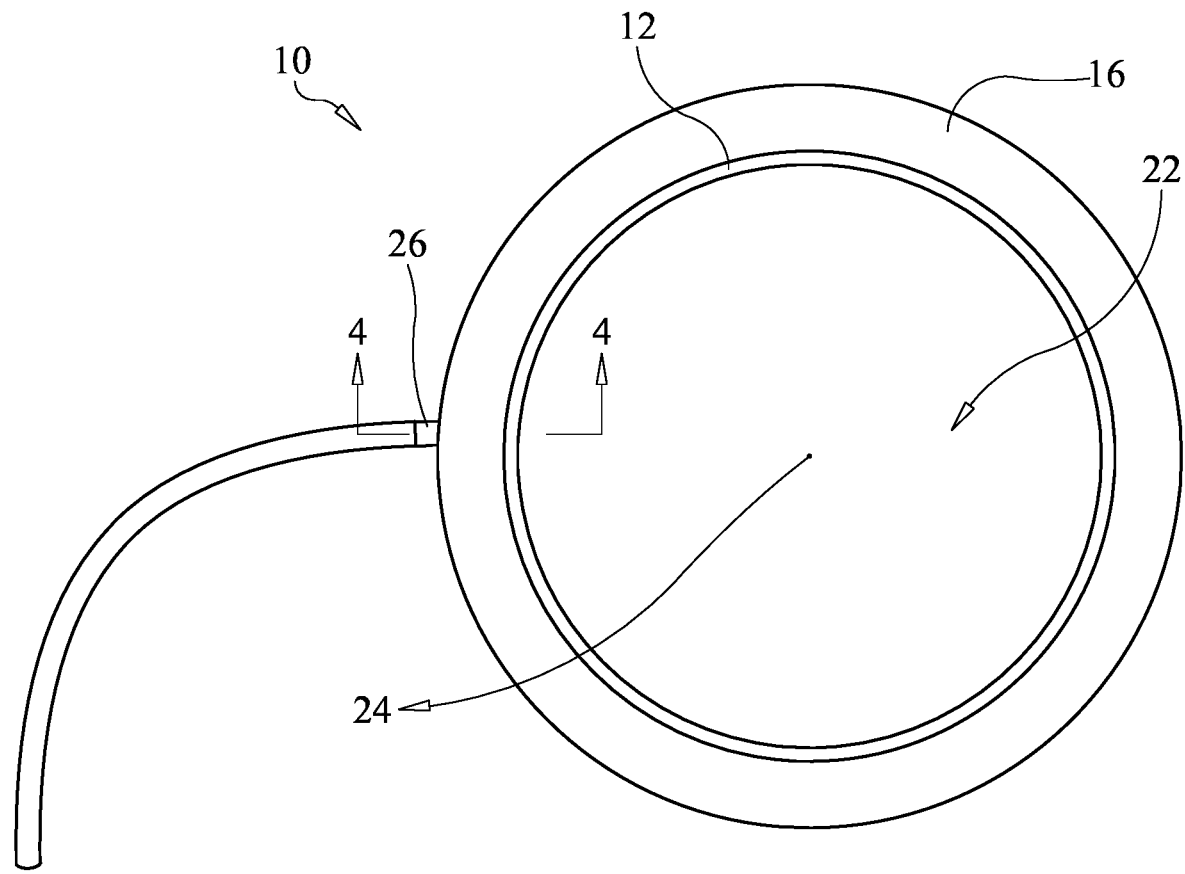
FIG. 3 is top view of the surgical retractor of FIG. 1.

The following detailed description of embodiments of the invention references the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail. The embodiments are intended to describe aspects of the invention in sufficient detail to enable those skilled in the art to practice the invention. Other embodiments can be utilized, and changes can be made without departing from the scope of the disclosure.

In FIG. 1, there is illustrated a surgical retractor 10 in accordance with an embodiment of the invention. Surgical retractor 10 has a first end 12, a second end 14, and a middle portion 15. The first end 12, representatively the proximal end, comprises an inflatable annular ring 16 and the second end 14, representatively the distal end, comprises an inflatable annular ring 18. The middle portion 16 comprises a flexible sheath 20 that is attached to rings 16 and 18 and extends a length therebetween. An access opening 22 extends through the rings 16 and 18 and the sheath 20 along a longitudinal axis 24 extending through the distal and proximal ends.

Rings 16 and 18 are each configured such that the rings are inflatable and when inflated the rings expand in the radial direction as taken from axis 24 with no to minimal expansion in the axial direction (i.e., along axis 24). Stated differently, when rings are inflated the diameter of each ring increases without or with minimal increase to the longitudinal cross-sectional area thereof (i.e., the thickness of the ring). Rings 16 and 18 may be constructed of a two way stretch material to provide the desired inflation in the radial direction while constraining inflation in the axial direction.

In the representatively illustrated embodiment, ring 16 has an inflation port 26 that is used to fluidically connect the ring to a source of fluid for inflation and ring 18 is fluidically connected to ring 16 by lumen tube 28. As shown, a syringe 30, filled with water, is connected to port 26 via tubing 32. Rings 16 and 18 are inflated to increase their diameter by operating the syringe and inflating the rings with the water. Other inflating devices could be used to inflate and deflate the rings. Further, it is contemplated that the rings could be fluidically isolated from each other and inflated independently.

Further, in the representative illustrated embodiment, rings 16 and 18 are circular shaped and are of the same size. However, rings 16 and 18 may be circular, ovoid, rectangular, square, or have other polygon shapes. Further, rings 16 and 18 may be symmetrical or asymmetrical shaped and/or dimensioned.

Sheath 20 is constructed of a two way stretch material with the material oriented such that the sheath may stretch in the radial direction in relation to axis 24 but will not stretch in the axial direction between rings 16 and 18. The purpose is to allow the sheath to expand radially along with radial expansion of the rings without increasing the distance between the rings to provide tissue and bone retraction force by the sheath.

Figure 4:
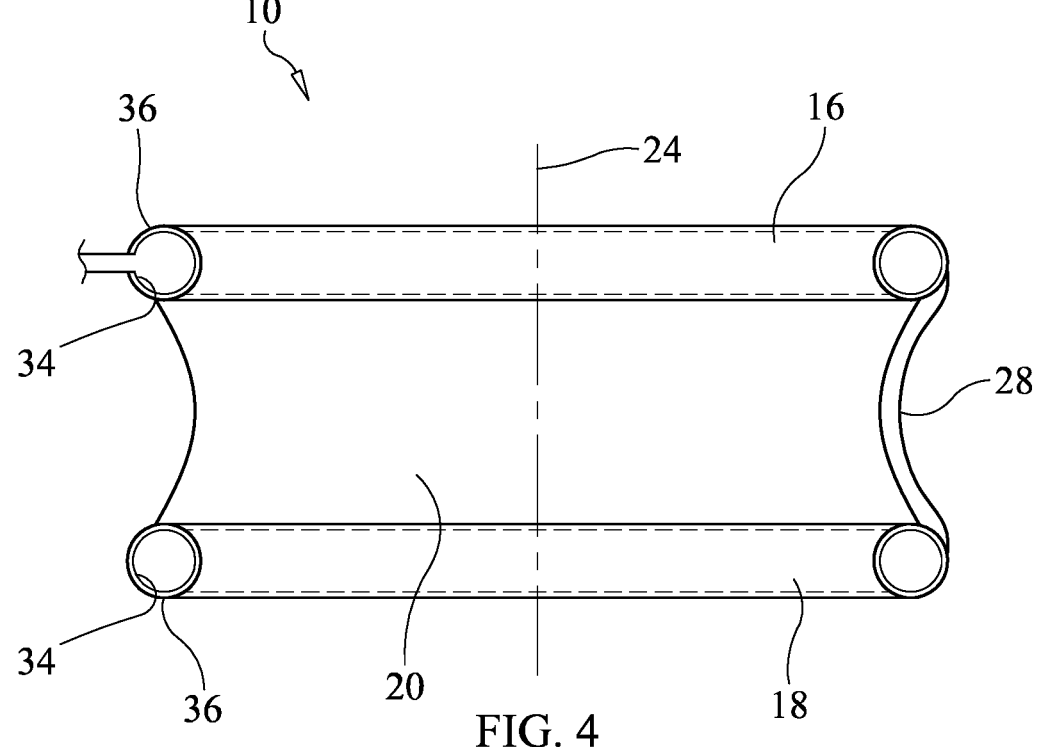
FIG. 4 is a cross-sectional view of the surgical reactor of FIG. 1 taken along line 4-4 in FIG. 3 and showing a first arrangement with inflatable tubes.

FIG. 4 is a cross section of an embodiment of retractor 10. As illustrated in this embodiment, each ring 16 and 18 may comprise an inner, inflatable tube 34 that is encased or otherwise enclosed within an exterior covering 36. Exterior covering 36 may be constructed of two-way stretch fabric with the fibers of the fabric oriented to allow the covering to radially expand relative to axis 24 but prevent the fabric from expanding in a direction axially along axis 24 with inflation of the tubes 34.

Figure 5:
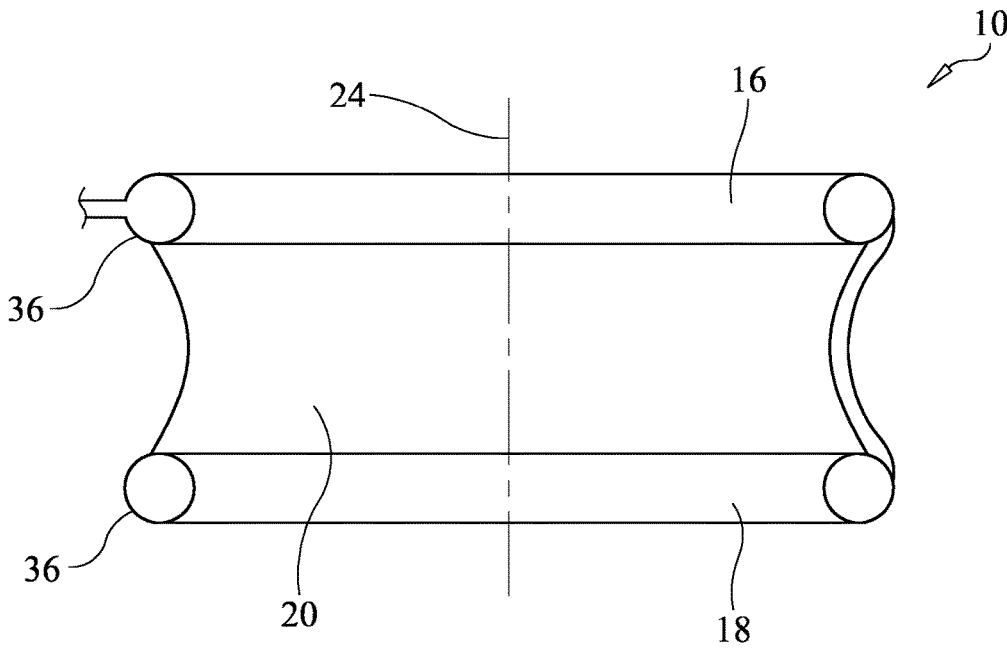
FIG. 5 is a cross-sectional view like FIG. 4, showing a second arrangement without inflatable tubes.

FIG. 5 is a cross section of another embodiment of retractor 10. As illustrated in the embodiment, each ring 16 and 18 may not have the inflatable tube as shown in FIG. 4. Rather, the material forming the rings may be coated with a material that provides the ring construction impermeable to water, thereby permitting inflation without requiring an inner tubing. Like previously, the fabric material forming the rings 16 and 18 may be constructed of two-way stretch fabric with the fibers of the fabric oriented to allow the rings to radially expand relative to axis 24 but prevent the rings from expanding in a direction axially along axis 24 with inflation.

Figure 6:
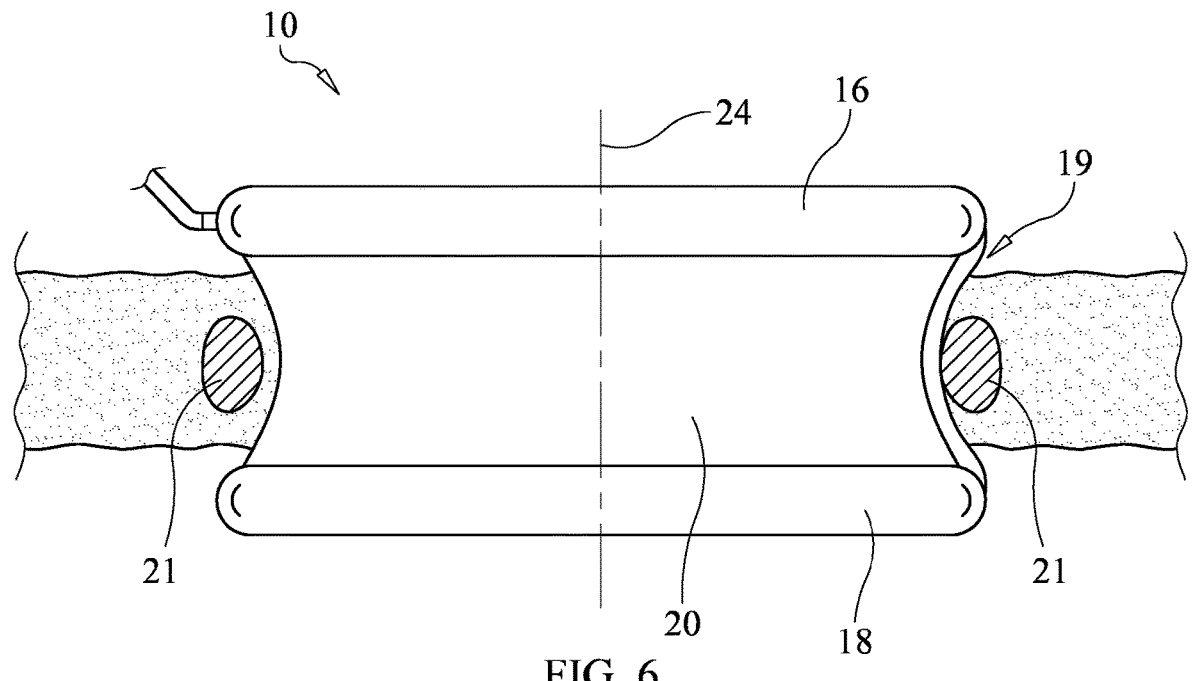
FIG. 6 is a diagrammatic cross-sectional view showing a surgical retractor in use, disposed within an incision made in a patient.

With reference to FIG. 6, surgical retractor 10 is representatively shown in use, inserted into a thoracic incision 19 and between ribs 21 of a patient. As rings 16 and 18 are radially expand by inflating them with water, the sheath 20 radially expands along with the rings and contacts the patient's soft tissue and ribs, thereby pushing them apart and creating a space for surgical visualization and instrumentation. The extent of rib retraction can be adjusted by adding or removing water to the rings 16 and 18. The benefit here is a less traumatic mechanism to apply the force required to spread the ribs. The force required to spread the ribs is distributed by the sheath over a larger cross-sectional of tissue and bone than traditionally available rib retractors.

Figure 7:
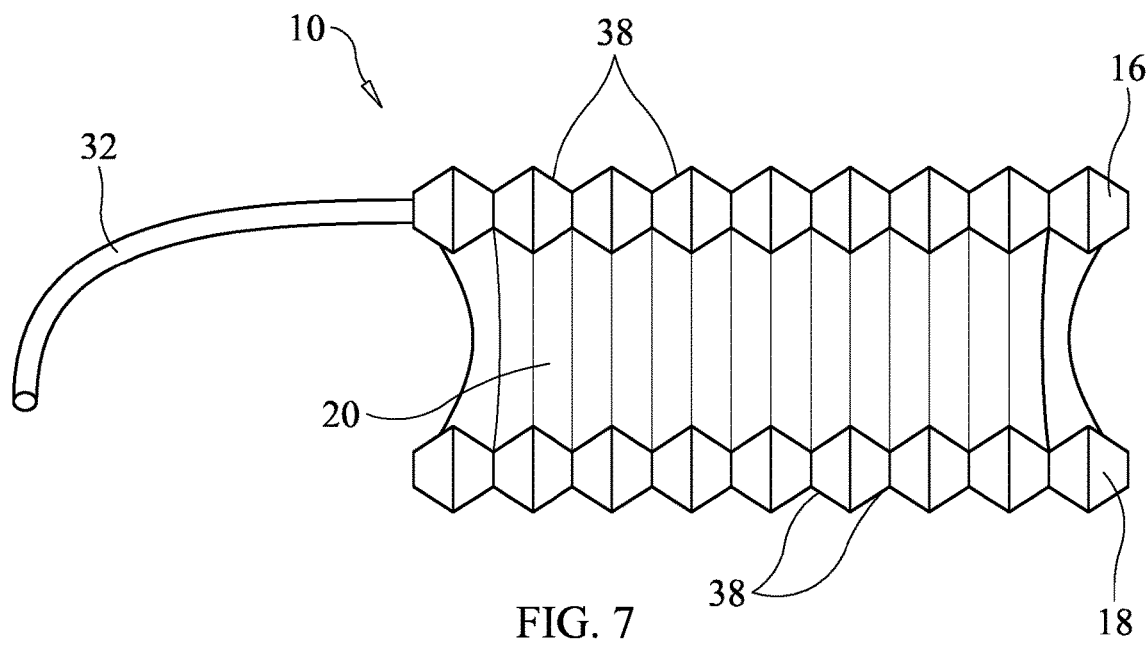
FIG. 7 is a side view of a surgical retractor shown in accordance with another embodiment of the invention.
Figure 8:
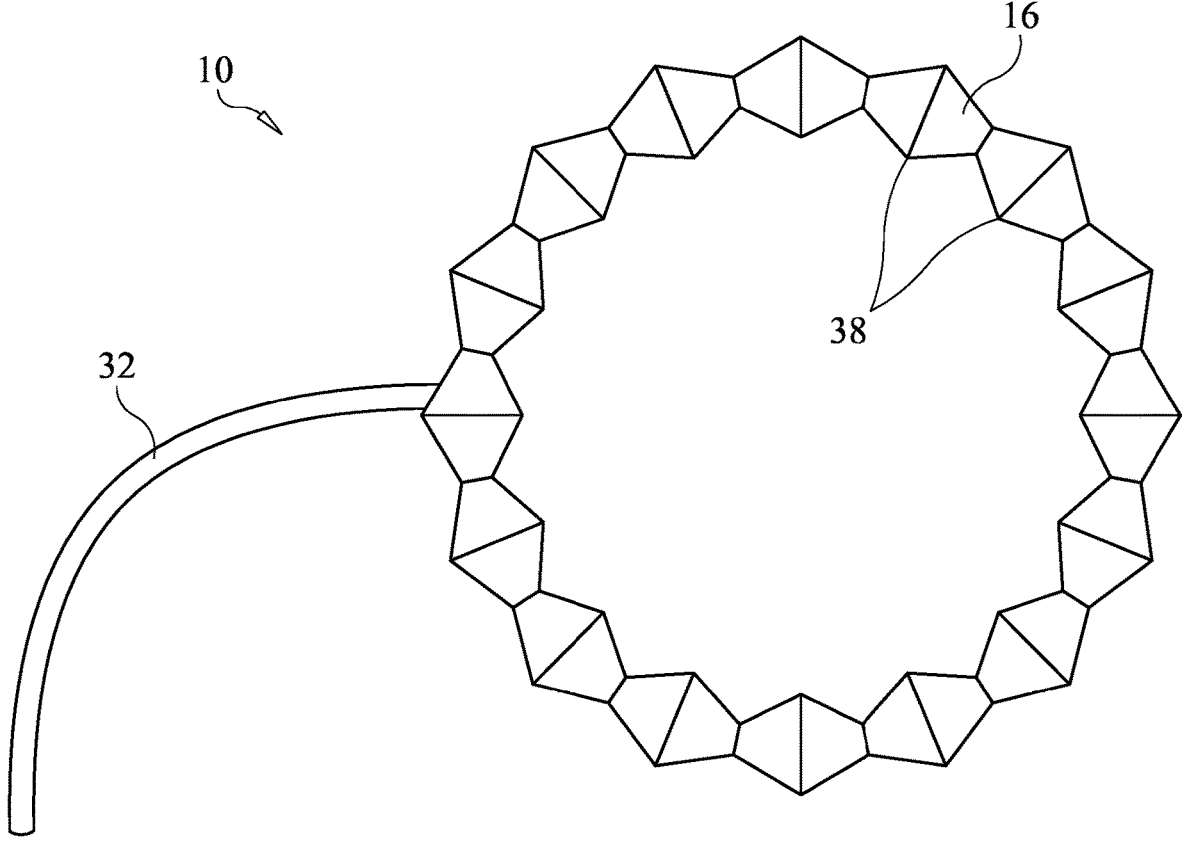
FIG. 8 is a top view of the surgical retractor of FIG. 7.

With reference to FIGS. 7 and 8, in an embodiment, rings 16 and 18 may have a pleated construction having a plurality of pleats 38 along the length of the rings. Pleats 38 may be constructed to allow the rings to radially expand relative to axis 24 but prevent the rings from expanding in a direction axially along axis 24 with inflation. Rings 16 and 18 may be constructed such that only the pleats provide the desired radial expansion. Rings 16 and 18 may be constructed such that the pleats combined with two-stretch fabric, forming the rings, provide the desired radial expansion. Rings 16 and 18 may have the inner tube construction or may have the tubeless construction shown in FIGS. 4 and 5, respectively, and discussed above.

Figure 9:
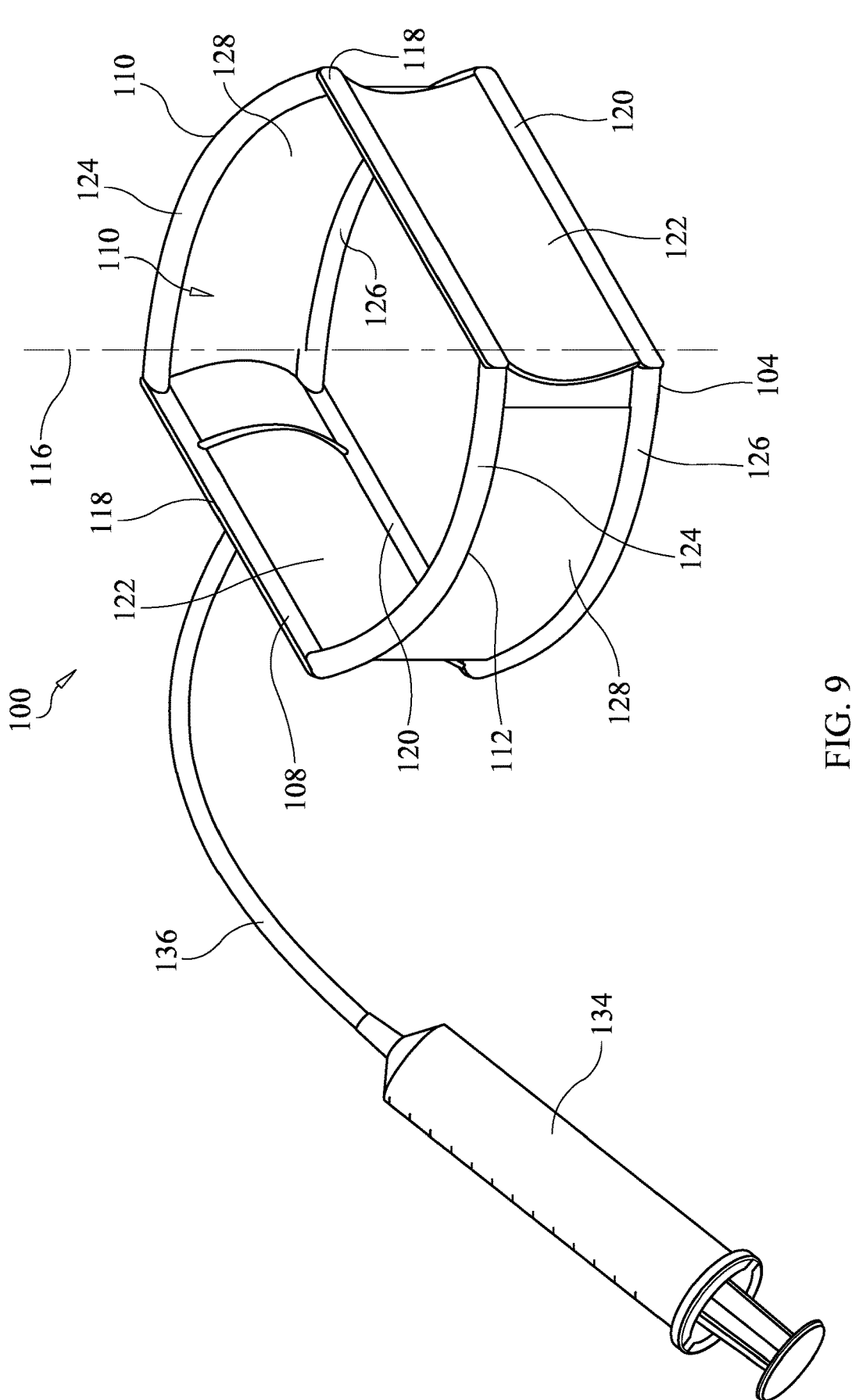
FIG. 9 is a perspective view of a surgical retractor shown in accordance with another embodiment of the invention.
Figure 10:
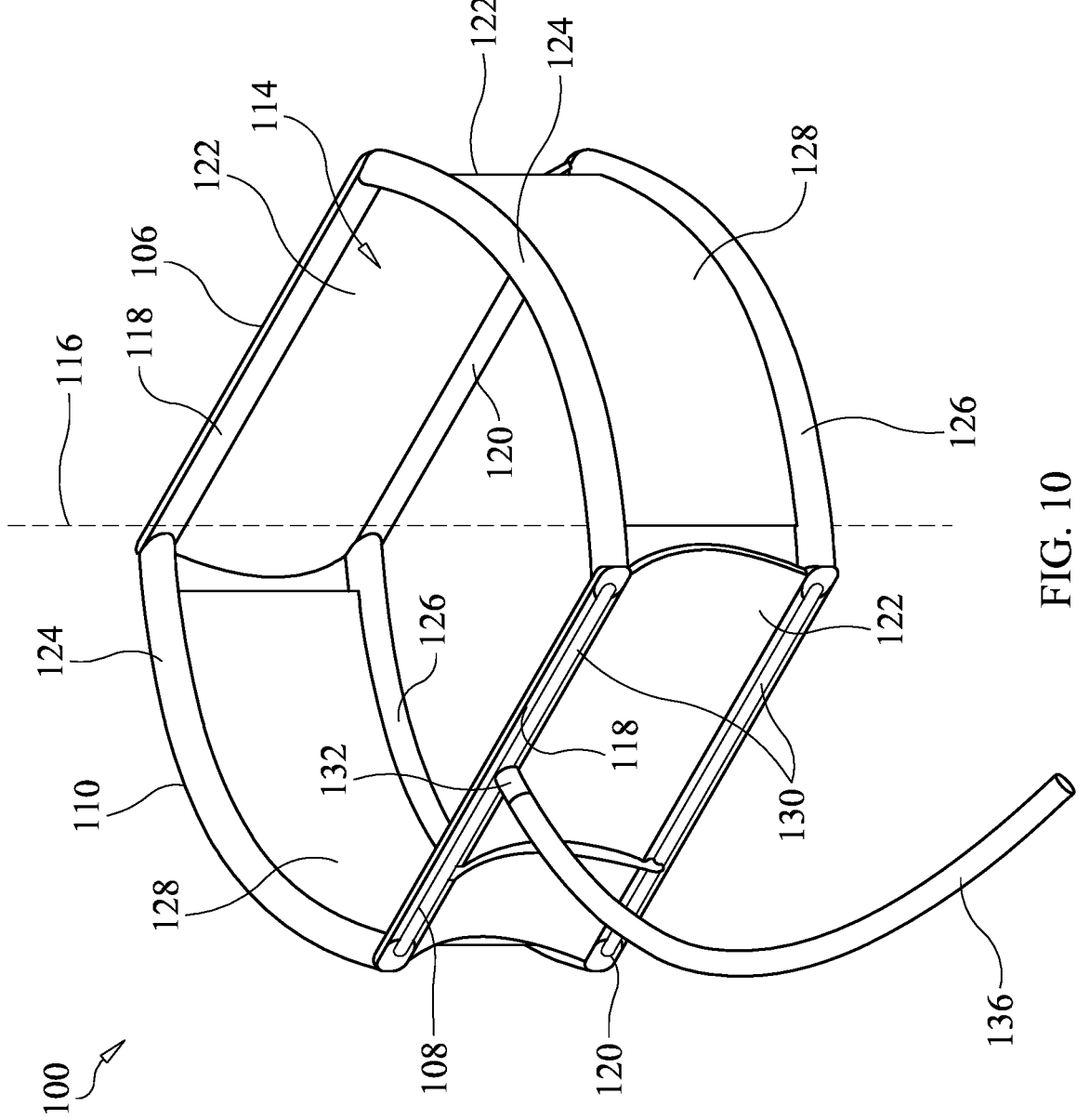
FIG. 10 is a second perspective view of the surgical retractor of FIG. 9.

With reference to FIGS. 9 and 10, there is shown a surgical retractor 100 in accordance with another embodiment of the invention. Retractor 100 has a similar construction to retractor 10 but is constructed so that retractor expansion occurs in controlled direction relative to the surgical incision. As shown in the representatively illustrated embodiment, reactor 100 has a proximal end 102, a distal end 104, non-expanding sides 106 and 108 and expanding sides 110 and 112. An access opening 114 extends through the ends 102 and 104 along a longitudinal axis 116. Non-expanding sides 106 and 108 are arranged on opposite sides and expanding sides 110 and 112 are arranged on opposite sides and extend between the non-expanding portions.

Retractor 100 is configured such that the non-expanding side would be placed in an incision between a pair of ribs with an orientational such that each non-expanding side extend along a length of a respective rib with the expanding sides extending between the ribs.

Non-expanding sides 106 and 108 may be constructed from various rigid materials such as but not limited to plastics and metals. Each non-expanding sides 106 and 108 may have spaced upper and lower elements 118 and 120 and an intermediate element 122 extending therebetween. The intermediate element 122 may be concaved in a direction inwardly to receive and seat a rib therein.

Each expanding side 110 and 112 may have an upper (proximal) inflatable member 124 and a lower (distal) inflatable member 126 and a section of material 128 extending therebetween and along lengths thereof. Like rings 16 and 18 discussed above, members 124 and 126 are constructed so that expansion is restrained along a desired direction. Particularly, members 124 and 126 are constructed such that when inflated their respective lengths extend without appreciable expansion in thickness. That is, when members 124 and 126 are inflated they increase the space or distance between the non-expanding sides to provide surgical retract force against the ribs upon which the non-expanding side press against. Member 124 and 126 and material 128 may be constructed of a two way stretch material having its stretch fibers orientated to provide the desired directional inflation/extension of members 124 and 126.

In the representatively illustrated embodiment, members 124 and 126 of each side 110 and 112 may be fluidically connected by respective fluid lumens 130 which may have an inflation port 132 that is used to fluidically connect the ring to a source of fluid for inflation. As shown, syringe 134, filled with water, is connected to port 132 via tubing 136. Members 124 and 126 are inflated to increase their respective lengths by operating the syringe and inflating the members with the water. Other inflating devices could be used to inflate and deflate the members. Further, it is contemplated that the members could be fluidically isolated from each other and inflated independently.

One or more members 124 and 126 may have a similar construction to rings 16 and 18 as described above in connection with FIGS. 4 and 5. Further, one or more members 124 and 126 may have a pleated construction as described above in connection with FIGS. 6 and 7.

It will be appreciated by persons skilled in the art that the present embodiment is not limited to what has been particularly shown and described hereinabove. A variety of modifications and variations are possible considering the above teachings without departing from the scope of the disclosure.

What is claimed is:

1. A surgical retractor, comprising:

a proximal end, a distal end, a longitudinal axis defining an access opening extending through the proximal and the distal end;

first and second non-expanding sides arranged opposite from one another and having a space extending therebetween;

first and second expanding sides arranged opposite from one another and extending between the first and second non-expanding sides;

wherein each of the first and second expanding sides
being configured to be extensible to increase the space
between the first and second non-expanding sides;
wherein the first and second expanding sides includes a
first inflatable element disposed at the proximal end, a
second inflatable element disposed at the distal end,
and an intermediate portion extending between the first
and second inflatable elements and along a length of
each; and wherein the first and second inflatable ele-
ments configured to extend in length but not in thick-
ness when inflated; and
wherein the first inflatable element and the second inflat-
able element of one or both of the first and second
expanding sides comprises a two-way stretch fabric
material having stretch fibers oriented so as to permit
the expansion in length without the expansion in thick-
ness.

2. The surgical retractor of claim 1, wherein the interme-
diate portion of one or both of the first and second expanding
sides comprises a two-way stretch fabric material having
stretch fibers oriented so as to permit expansion of the
intermediate portion along a direction between the non-
expanding sides without expanding in a direction between
the first and second inflatable elements.

3. The surgical retractor of claim 1, wherein one or both
of the first and second inflatable members of one or both of
the first and second expanding sides comprise an inflatable
innertube enclosed in an exterior covering.

4. The surgical retractor of claim 3, wherein the exterior
covering comprises a two-way stretch fabric material having
stretch fibers oriented so as to permit the expansion in length
without the expansion in thickness.

5. The surgical retractor of claim 1, wherein first and
second non-expanding sides are constructed of a rigid mate-
rial.

6. A surgical retractor, comprising:
a proximal end, a distal end, a longitudinal axis defining
an access opening extending through the proximal and
the distal end;
first and second non-expanding sides arranged opposite
from one another and having a space extending ther-
ebetween;
first and second expanding sides arranged opposite from
one another and extending between the first and second
non-expanding sides;
wherein each of the first and second expanding sides
being configured to be extensible to increase the space
between the first and second non-expanding sides;
the first and second expanding sides includes a first
inflatable element disposed at the proximal end, a
second inflatable element disposed at the distal end,
and an intermediate portion extending between the first and second inflatable elements and along a length of
each; and wherein the first and second inflatable ele-
ments configured to extend in length but not in thick-
ness when inflated; and
the first inflatable element and the second inflatable
element of the first and second expanding sides com-
prises a two-way stretch fabric material having stretch
fibers oriented so as to permit the expansion in length
without the expansion in thickness.

7. The surgical retractor of claim 6, wherein one or both
of the first and second inflatable members of one or both of
the first and second expanding sides comprise an inflatable
innertube enclosed in an exterior covering.

8. The surgical retractor of claim 7, wherein the exterior
covering comprises the two-way stretch fabric material.

9. The surgical retractor of claim 6, wherein first and
second non-expanding sides are constructed of a rigid mate-
rial.

10. A surgical retractor, comprising:
a proximal end, a distal end, a longitudinal axis defining
an access opening extending through the proximal and
the distal end;
first and second non-expanding sides arranged opposite
from one another and having a space extending ther-
ebetween;
first and second expanding sides arranged opposite from
one another and extending between the first and second
non-expanding sides;
wherein each of the first and second expanding sides
being configured to be extensible to increase the space
between the first and second non-expanding sides;
wherein the first and second expanding sides includes a
first inflatable element disposed at the proximal end, a
second inflatable element disposed at the distal end,
and an intermediate portion extending between the first
and second inflatable elements and along a length of
each; and wherein the first and second inflatable ele-
ments configured to extend in length but not in thick-
ness when inflated; and
wherein one or both of the first and second inflatable
members of one or both of the first and second expand-
ing sides comprise an inflatable innertube enclosed in
an exterior covering.

11. The surgical retractor of claim 10, wherein the exterior
covering comprises a two-way stretch fabric material having
stretch fibers oriented so as to permit the expansion in length
without the expansion in thickness.

12. The surgical retractor of claim 10, wherein first and
second non-expanding sides are constructed of a rigid mate-
rial.

* * * * *